United States Patent
Sabio Rey (10) Patent No.: US 7,557,146 B2
(45) Date of Patent: Jul. 7, 2009

(54) METHOD OF PREPARING LYCOPENE-ENRICHED FORMULATIONS THAT ARE FREE OF ORGANIC SOLVENTS, FORMULATIONS THUS OBTAINED, COMPOSITIONS COMPRISING SAID FORMULATIONS AND USE OF SAME

(76) Inventor: Eduardo Sabio Rey, C/ Gonzalo de Mafra, No. 11, Badajoz (ES) 06011

( * ) Notice: Subject to any disclaimer, the term of this patent is extended or adjusted under 35 U.S.C. 154(b) by 0 days.

(21) Appl. No.: 11/911,765

(22) PCT Filed: Mar. 9, 2006

(86) PCT No.: PCT/ES2006/000114

§ 371 (c)(1),
(2), (4) Date: Oct. 17, 2007

(87) PCT Pub. No.: WO2006/111591

PCT Pub. Date: Oct. 26, 2006

(65) Prior Publication Data

US 2008/0194703 A1    Aug. 14, 2008

(30) Foreign Application Priority Data

Apr. 19, 2005  (ES) ................ 200500934

(51) Int. Cl.
*A61K 31/01* (2006.01)
(52) U.S. Cl. .................... 514/762; 426/655
(58) Field of Classification Search .......... None
See application file for complete search history.

(56) References Cited

U.S. PATENT DOCUMENTS

| 5,837,311 A | 11/1998 | Zelkha et al. |
| 5,897,866 A | 4/1999 | Bombardelli et al. |
| 6,605,296 B1 * | 8/2003 | Stuckler .................... 424/439 |
| 2003/0180435 A1 | 9/2003 | Shi |
| 2004/0024275 A1 | 2/2004 | Vuong |
| 2004/0131733 A1 | 7/2004 | Rey et al. |
| 2005/0153038 A1 | 7/2005 | Giori |

FOREIGN PATENT DOCUMENTS

| EP | 0671461 | 9/1995 |
| EP | 0818225 | 1/1998 |
| EP | 1103579 | 5/2001 |

(Continued)

OTHER PUBLICATIONS

Garti et al. JAOCS, vol. 81, No. 9, pp. 873-877, 2004.*

(Continued)

*Primary Examiner*—Deborah D Carr
(74) *Attorney, Agent, or Firm*—Katten Muchin Rosenman LLP (57) ABSTRACT

The present invention refers to a process to obtain a lycopene-enriched formulation free of organic solvents that comprises: (a) mixing a lycopene source with an extractant lipid, and (b) separating the lipidic phase obtained in step (a) to obtain the lycopene-enriched formulation free of organic solvents; in which the mixture in step (a) is carried out in the absence of organic solvents. The invention also refers to the formulations obtained in this way and to compositions that comprise them. These formulations and compositions have antioxidant properties and are useful to manufacture nutraceutical, cosmetic, pharmaceutical or food products.

15 Claims, 2 Drawing Sheets

FOREIGN PATENT DOCUMENTS

| | | |
|---|---|---|
| EP | 1384472 | 1/2004 |
| EP | 1 487 282 | 5/2006 |
| ES | 2183471 | 3/2003 |
| JP | 2002125619 A | 5/2002 |
| WO | 9613178 | 5/1996 |
| WO | 9748287 | 12/1997 |
| WO | 0240003 | 5/2002 |

OTHER PUBLICATIONS

Inventors Remarks, Apr. 10, 2008.

Sanjiv Agarwal, et al., "Tomato lycopene and its role in human health and chronic diseases", Sep. 19, 2000, pp. 739-744, Canadian Medical Association.

V. Bohm, et al., Intestinal absorption of lycopene from different types of oleoresin capsules:, 2002, vol. 67, pp. 1910-1913, Institute of Food Technologies.

Graham W. Burton, "Antioxidant action of carotenoids", Sep. 12, 1998, pp. 109-111, American Institute of Nutrition.

S.L. De Felice, "The Nutraceutical initiative a proposal for economic and regulatory reform", Apr. 1992, pp. 77-79, Food Technology.

Paolo Di Mascio, et al., "Antioxidant defense systems: the role of carotenoids, tocopherols, and thiols", 1991, pp. 194-200, American Society for Clinical Nutrition.

Paolo Di Mascio, et al., "Lycopene as the most efficient biological carotenoid singlet oxygen quencher", 1989, pp. 532-538, vol. 274, No. 2, Archives of Biochemistry and Biophysics.

Anthony T. Diplock, "Antioxidant nutrients and disease prevention: an overview", 1991, pp. 189-193, vol. 53, American Society for Clinical Nutrition.

Edward Giovannucci, et al., "Intake of carotenoids and retinol in relation to risk of prostrate cancer", Dec. 6, 1995, pp. 1767-1776, vol. 87, No. 23, Journal of National Cancer Institute.

Edward Giovannucci, "Tomatoes, tomato-based products, lycopene, and cancer: Review of the epidemiologic literature", Feb. 17, 1999, pp. 317-331, vol. 91. No. 4, Journal of the National Cancer Institute.

Edgar R. Miller, et al., "Meta-analysis: High-dosage vitamin e supplemenation may increase all-cause mortality", Annals of Internal Medicine, 2005, pp. 37-47, vol. 142. No. 1, American College of Physicians.

Marlene M. Most, "Estimated phytochemical content of the dietary approaches to stop hypertension (DASH) diet is higher than in the control study diet", 2004, pp. 1725-1727, American Dietetic Association.

Sheldon R. Pinnell, "Cutaneous photodamage, oxidative stress, and topical antioxidant protection" 2003, pp. 1-22, vol. 48. No. 1, J Am Acad Dermatol.

E. Sabio, "Lycopene and b-carotene extraction from tomato processing waste using supercritical $CO_2$", Ind. Eng. Chem. Res., Nov. 6, 2003, pp. 6641-6646, vol. 42. No. 25, American Chemical Society.

Kumarasamy Senthil, et al., "Evidence of oxidative stress in circulation of ovarian cancer patients", 2004, pp. 27-32, Clinica Chimica Acta 339.

Wilhelm Stahl, et al. "Perspectives in biochemistry and biophysics", pp. 1-9, vol. 336. No. 1, Dec. 1, 1996, Archives of Biochemistry and Biophysics.

Shyinya Toyokuni, et al., "Persistent oxidative stress in cancer", 1995, pp. 1-3, Federation of European Biochemical Societies.

Karin Wertz, et al., "Lycopene: modes of action to promote prostate health", May 25, 2004, pp. 127-134, Archives of Biochemistry and Biophsysics.

Dr. J. M. Sune Negre, "Capsulas de gelatina blandas" Tratado de Farmacia Galencia, 1993, pp. 587-592, 1a ed., Luzan 5, S.A. de Ediciones, Spain.

International Search Report dated Jun. 20, 2006 from the corresponding PCT/ES2006/000114.

Sabio E., Lozano M., Montero de Espinosa V., Coelho V.J., Pereira A. P., and Palavra A.F. (2003), "Lycopene and other carotenoids extraction from tomato waste using supercritical $CO_2$", Ind. Eng. Chem. Res., 42, 6641-6646).

* cited by examiner

METHOD OF PREPARING LYCOPENE-ENRICHED FORMULATIONS THAT ARE FREE OF ORGANIC SOLVENTS, FORMULATIONS THUS OBTAINED, COMPOSITIONS COMPRISING SAID FORMULATIONS AND USE OF SAME

FIELD OF THE INVENTION

The invention refers to the field of lycopene-enriched formulations, more specifically to lycopene-enriched formulations free of organic solvents, to the process to obtain them and to compositions comprising said formulations. These formulations and compositions are useful to make nutraceutical, cosmetic, pharmaceutical or food products.

BACKGROUND OF THE INVENTION

Lycopene is a carotenoid with 40 carbon atoms, which is responsible for the red colour of many fruits and vegetables. From a chemical perspective, lycopene is an isoprenoid hydrocarbon consisting of 8 units of isoprene forming a symmetrical chain. Its structure contains 11 conjugated double bonds and 2 non-conjugated ones. Therefore, it has a greater number of double bonds than any other carotenoid, including β-carotene. This unusual structure confers it some special characteristics. Hence, for example, lycopene can be used as a coloring or dye and is much more efficient as a pigment than β-carotene. Hence, it is noteworthy that lycopene covers a broader colour range, that going from yellow, passing through orange, to an intense red color. Moreover, it has a stronger colour intensity in the yellow-orange colour range, 6 to 8 times greater than that of β-carotene. Its use as a food coloring has been authorized, and its European code is E-160d. However, its use today is not very widespread owing to its high price.

Although the use of lycopene as a coloring is interesting, undoubtedly its most noteworthy property is its antioxidant capacity. In the organism, oxidations occur on a cellular level due to the presence of free radicals and, especially, the singlet oxygen. These undesirable reactions are highly dangerous since, like other radical reactions, they are autocatalytic, i.e. they are self-propagated via a chain reaction process. This can produce irreversible damage in essential cell components (membrane lipids, nucleic acids etc.) in a process known as oxidative stress that is associated with cellular ageing, degenerative diseases, blocking of arteries and the appearance of different types of cancer (S. Toyokuni, K. Okamoto, J. Yodoi and H. Hiai (1995), "Persistent oxidative stress in cancer", *FEBS Letters*, Volume 358(1), 1-3; K. Senthil, S. Aranganathan and N. Nalin (2004), "Evidence of oxidative stress in the circulation of ovarian cancer patients", *Clinica Chimica Acta*, 339(1-2), 27-32).

Lycopene has a high antioxidant potential (Burton G. W. (1989), "Antioxidant action of carotenoids", *J. Nutr.* 119, 109-111; Diplock A. T. (1991), "Antioxidant nutrients and disease prevention: an overview", *Am. J. Clin. Nutr.* 53, 189S-193S; Wertz K., Siler U. and Goralczy R. (2004), "Lycopene: modes of action to promote prostate health", *Archives of Biochemistry and Biophysics*, 430(1), 127-134) that makes it an excellent inactivator of the singlet oxygen and free radicals (Di Mascio P., Murphy M. E. and Sies H. (1989), "Lycopene as the most efficient biological carotenoid singlet oxygen quencher", *Arch. Biochem Biophys.*, 274, 532-538; Di Mascio P., Murphy M. E. and Sies H. (1991), "Antioxidant defense systems: The role of carotenoids, tocopherols and thiols", *Am. J. Clin. Nutn.*, 53, 1945-2005). This natural pigment acts as an antioxidant agent, transferring electrons to the free radicals, deactivating them. The lycopene radical formed is stable owing to its large number of double bonds, which permit it to stabilize by resonance. This antioxidant potential confers it an anticarcinogenic activity and a preventive action against cardiovascular diseases. The studies of Giovannucci et al. (Giovannucci E. (1998), "Tomatoes, tomato-based products, Lycopene, and cancer: Review of the epidemiologic literature" 1999, *J. Nat. Cancer Inst.*, vol 91, 317-331; Giovannucci E., Ascherio A., Rimm E. B., Stampfer M. J., Colditz G. A. and Willett W. C. (1995), "Intake of carotenoids and retinol in relation to risk of prostate cancer", *J. Natl. Cancer. Inst.*, 87, 1767-1776), indicate that consumption of tomatoes, tomato sauce and pizza is directly associated with a reduced risk of developing different types of cancer, such as cancers of the digestive system and prostate cancer.

Cardiovascular diseases are among the most common causes of death in western countries. It was initially considered that one of the main risk factors corresponded to the presence of high blood cholesterol levels. Later, it was suggested that the key step in atherogenesis is oxidation of cholesterol by the action of free radicals. It has been shown that the incidence of cardiovascular diseases is strongly correlated with plasma levels of carotenoids, and lycopene is especially effective at clearing away peroxide radicals under physiological conditions and preventing the oxidation of low molecular weight lipoproteins (LDL) to their atherogenic form.

More recently, the possible preventive effect of lycopene against diseases such as diabetes type II and osteoporosis has been studied. It appears that oxidative processes are also involved in these diseases, thus lycopene could also have a beneficial effect here.

Because of its remarkable properties, lycopene is also a true nutraceutical product. A nutraceutical product can be defined as "a food product, or part of a food, that confers medical or health benefits, including the prevention and treatment of diseases" (De Felice S. L. (1991), "The nutraceutical initiatives: A proposal for economic and regulatory reform", Ed. *The Foundation for Innovation in Medicine*).

Lycopene is presented on the market as a solid, as crystalline lycopene dispersed in a liquid in which it is insoluble (water, ethanol or polyoles) or as an oleoresin.

Numerous patents and patent applications described how to obtain lycopene and lycopene-enriched products. Probably, patent application WO 96/13178 has had the greatest industrial application. This patent is noteworthy for its simplicity since it describes a process for preparing a lycopene concentrate by reducing the size of the lycopene crystals (present in the chromoplasts) in a medium which essentially does not dissolve lycopene (water, ethanol or polyoles). In other words, this method is based on using polar solvents, that do not dissolve lycopene (apolar compound) but, that "literally" pull with them the crystals that are present naturally in the plant chromoplasts. However, to obtain a lycopene-rich oleoresin, in this patent WO 96/13178 organic solvents are used, specifically acetone and ethyl acetate. In fact, all the oleoresins currently on the market are prepared using organic solvents, since these solubilise the apolar substances. The organic solvents most used include hexane, acetone and ethyl acetate (see, for example, the documents EP 671461 A1, EP 1487282 A1, EP 1103579 B1, EP 0818225, WO 97/48287, U.S. Pat. No. 5,837,311). Since organic solvents present some degree of toxicity, both for the workers handling these products and also for consumers it is recommendable not to use organic solvents to make nutraceutical products or products of pharmacological interest, since their total removal cannot be guaranteed. Neither does the use of synthetic lycopene ensure the absence of organic solvents, because they are used in the synthesis process.

Since lycopene is an apolar substance, it is also soluble in supercritical fluids (Sabio E., Lozano M., Montero de Espinosa V., Coelho V. J., Pereira A. P., and Palabra A. F. (2003), "Lycopene and other carotenoids extraction from tomato waste using supercritical $CO_2$", *Ind. Eng. Chem. Res.*, 42, 6641-6646). Recently, a patent application was presented (WO 02/40003) based on the extraction of lycopene using supercritical $CO_2$. After the supercritical extraction, the mixture is depressurized, and $CO_2$ passes to the gaseous state, obtaining an extract rich in lycopene free of solvents. This method clearly presents some advantages compared to the use of organic solvents. However, it is noteworthy that the process is considerably more expensive. Moreover, because of the greenhouse effect of $CO_2$, precautions must be taken to avoid emitting this compound.

With the new invention presented here, lycopene-rich products can be obtained without using any intermediate chemical agent, organic solvents, supercritical fluids or dispersants.

The classical approach, to date, to obtain lycopene-enriched formulations has focused on obtaining oleoresins from a lycopene-enriched product by extraction with an organic solvent, the presence of which is not desirable in the final formulation. After carrying out the extraction, the organic solvent is eliminated (although never completely) and the extract obtained is diluted in oil or fat that is used in the final formulation.

The present inventors have now developed an alternative process to obtain lycopene-enriched formulations by direct solubilization, based on the liposoluble nature of the lycopene. This process directly produces the desired formulation without using organic solvents or other intermediate chemical agents, supercritical fluids or dispersants, for example, as mentioned previously.

Moreover, this direct solubilization process allows to obtain in a simple and inexpensive way, lycopene-enriched formulations with an appropriate contents of lycopene (of around 500-1000 ppm) to permit it to be dosified easily and safely. Indeed, the lycopene-enriched formulations known in the state of the art of the technique have much higher lycopene concentrations (30,000-60,000 ppm) making it very difficult for these to be dosed for regular and controlled intake. Recent studies suggest that a high intake of antioxidants may not merely not be beneficial but may even be harmful, since their antioxidant action depends on their concentrations, and high concentrations may no longer be antioxidant but can become pro-oxidants (E. R. Miller, R. Pastor-Barriuso, D. Dalal, R. A. Riemersma, A. Appel and E. Guallar (2005); "Meta-Analysis: High-dosage vitamin E supplementation may increase all-cause mortality". *Ann Intern Med.* 142: 37-46).

In this new process, a starting material rich in lycopene is directly exposed to the solubilising action of an oil or fat that is to be used in the final formulation, obtaining, in a simple and rapid way a lycopene-enriched product with the appropriate proportion of lycopene that can be easily and safely administered without using any intermediate chemical agent. That is, the preparation of this product only uses the lycopene source and the oil or fat to be present in the final formulation or, in other words, the product obtained is exempt from any organic solvent or chemical agent that is strange to the final formulation.

Moreover, when the extractant lipid is an edible oil or fat, the resulting solid residue produced after the extraction can be consumed, since it has not been treated with organic solvents.

Therefore, its advantages over the conventional indirect method mentioned previously that uses organic solvents, are numerous, as any skilled person in the art can easily deduce. These correspond to:

1) An absence of chemical pollutants, mainly organic solvents, hence the formulation obtained has a greater added value.

2) A simpler process: less costs, greater rapidity, less components used in the process, less energy consumption, less steps required to obtain the final formulation, etc.

3) Adequate lycopene content: easy and safe to dosify, direct consumption of the product in any form of presentation.

4) Less environmental pollution. The organic solvents are pollutants as well as the gases used in the supercritical fluids.

5) Nutritionally more beneficial formulations than those obtained by simply mixing pure lycopene with the oil or fat: additional content of other extracted phytochemicals (carotenoids, sterols, etc.) with antioxidant potential and synergic action between them, increased when using olive oil as an extractant lipid (rich in tocopherols). Additionally, these phytochemicals are undegraded, in contrast to those extracted by the extraction technique using solvents, in which the aggressive treatments used to eliminate the solvent notably degrade all the phytochemicals, including lycopene.

6) The solid residue that remains after the extraction has a high added value, since it has not undergone any chemical treatment and can be used directly to produce other products (sauces, creams, purees etc), having a high nutritional value and being a good source of soluble dietary fiber and minerals.

OBJECT OF THE INVENTION

Therefore, an object of the present invention is to provide a process to obtain a lycopene-enriched formulation free of organic solvents.

Likewise, another object of this invention is said lycopene-enriched formulation free of organic solvents.

An additional object of this invention is a composition that comprises said lycopene-enriched formulation free of organic solvents.

Finally, another object of this invention is the use of said formulations or said compositions to make nutraceutical, cosmetic, pharmaceutical or food products.

DETAILED DESCRIPTION OF THE INVENTION

Hence, the present invention provides a process to obtain a lycopene-enriched formulation free of organic solvents that comprises:

(a) mixing a lycopene source with an extractant lipid; and
(b) separating the lipidic phase obtained in step (a) to obtain the lycopene-enriched formulation free of organic solvents;

in which the mixture in step (a) is carried out in the absence of organic solvents.

In the context of the invention, the term "organic solvents" refers to chemical agents strange to the formulation, in other words, chemical compounds that are not required in the final formulation, but that are introduced during the process together with the lycopene source and the extractant lipid in order to enhance the extraction of lycopene.

The process to obtain this lycopene-enriched formulation free of organic solvents (herein referred to as the "process of the invention") can also be called direct solubilization. As mentioned previously, the method traditionally used to prepare oleoresins is an indirect method, in which the lycopene-enriched material is mixed with an organic solvent, the presence of which is not desired in the final formulation. After carrying out the extraction, the organic solvent is removed (although not completely) and the extract obtained is diluted in the oil or fat to be used in the final formulation.

The mixing operation in step (a) is carried out to interdisperse the solid (lycopene source) and the fluid (extractant lipid) in an attempt to facilitate the process of transferring the lycopene from one phase to another. The efficiency of this mass transfer process mainly depends on the efficacy of the degree of dispersion, rupture of the cell structure and the solubility of lycopene in the extractant lipid.

In a specific embodiment of the process of the invention, in step (a) the lycopene source and the extractant lipid are mixed by stirring at a high speed and at a temperature below 120° C. In a preferred embodiment, the speed of stirring ranges from 500 to 10000 r.p.m. and the temperature between 40 and 100° C. In another more preferred embodiment, the speed of stirring ranges from 2500 to 5000 r.p.m. and the temperature between 60 and 90° C.

Moreover, in step (a) the lycopene source and the extractant lipid can be mixed by other standard methods used in the food and pharmaceutical industries, such as homogenization at high pressure or hydro-shearing, microfluidification, ultrasound mixing, colloidal mill mixing etc.

According to this, there is a wide range of equipment and devices that can be used for this mixing process. Discontinuous mixers can be used such as tanks with a blade agitator or other structure connected to a rotating axle, or tanks with mobile blades (generally arranged at the base). Also, continuous mixers can be used in which the lycopene source or the extractant lipid are made to pass through a series of obstructions (perforated plates, wire grills, grids etc) by means of a screw transporter.

Similarly, high pressure homogenizers can be used, in which the lycopene source and the extractant lipid are made to pass at high speed and pressure through a narrow slit (which can be fed with a premixture of lycopene source/lipid or with two currents that flow into the entrance to the homogenizer); or hydro-shear homogenizers.

Analogously, in the mixing operation of step (a) other conventional devices can be used such as microfluidifiers, ultrasound devices, colloidal mills, etc.

After carrying out the mixing process the lipidic phase which constitutes the formulation object of the invention, must be separated. This phase will be constituted by the extractant lipid and the majority of the liposoluble compounds present in the lycopene source (triglycerides, colorants, antioxidants, etc.), including lycopene. This separation process can be carried out by any method of the art, such as decantation or by mechanical procedures such as centrifugation, for example. In a preferred embodiment, a decanter is used (horizontal centrifuge) that operates at a speed of 3000-4000 r.p.m. This type of versatile device that allows high yield productions of up to 6000 l/h, is used in olive oil manufacture and in drying of sludges, for example.

In a specific embodiment of the process of the invention, step (a) is carried out under vacuum or under an inert atmosphere. Indeed, optionally, when the extractant lipid used is easily oxidizable (for example, oils rich in polyunsaturated acids), it is recommendable to carry out step (a) under vacuum or under an inert atmosphere.

In another specific embodiment, the process of the invention comprises a previous dehydration step of the lycopene source.

A high moisture content can impede the process of direct solubilization. For example, fresh tomato has a moisture content of approximately 85% by weight, and under these conditions the extraction is almost zero. It is, therefore, necessary to reduce the moisture content of the lycopene source to a content below 75% by weight. Moreover, since the process of eliminating the water also involves cellular destruction, this previous dehydration of the lycopene source makes it unnecessary to carry out an enzymatic treatment to release the lycopene present inside the chromoplasts.

This dehydration can be total or partial, using a mechanical or thermal process traditionally used in the industry, such as, for example, centrifugation or evaporation. Additionally, enzymes or mechanical molturation can be used to destroy the cell structure and facilitate the release of lycopene from the chromoplasts, although, as mentioned, the dehydration process sufficiently destroys the cell structure.

In another specific embodiment, the lycopene-enriched formulation free of organic solvents obtained after step (b) can be submitted to a subsequent treatment to eliminate traces of water or solid residues that can remain, by filtration, centrifugation, decantation, etc.

In one specific embodiment of the process of the invention, the lycopene source or starting material is any plant product, algae or microorganism that contains lycopene.

In a preferred embodiment, the lycopene source is a plant product such as tomatoes, watermelons, wild berries, flowers etc. In an even more preferred embodiment, this plant product is a plant product derived from tomato selected from the group that comprises: completely dehydrated tomato, partially dehydrated tomato, tomato concentrate, powdered tomato and lyophilized tomato.

In particular, as a lycopene source, tomato concentrate from the tomato processing industry can be used, since this confers a series of important advantages:

1) The tomato concentrate is directly treated by the process of the invention without receiving any preliminary treatment.

2) The packaged tomato concentrate has a very long shelf life without requiring refrigeration. In fact, drums of concentrate are stored piled up at room temperature throughout the year until they are sold.

3) It is a process especially adapted to the tomato processing industry that could solve many problems currently faced by these industries. The benefits would lie in:
  a) Diversifying the products available. This is especially important in a sector that is almost exclusively centered around the production of tomato concentrate. For example, in Spain more than one million tonnes of tomatoes are processed and approximately 90% are used to make concentrate. A similar situation is found in the other tomato-producing countries, giving rise to an increased availability on the world market and a subsequent drop in prices.
  b) A more balanced use of the industrial facilities throughout the year. The production season for tomato concentrate is short (55-60 days), with 70% of the raw material received within one month. For the rest of the year the installations are hardly used. With the process of the invention, production activity could be maintained during the whole year.

c) Increased profits because of the two previous points and, especially, because the products obtained have a great added value.

d) Minimum investment since the companies in the sector are highly technological and therefore, for a low cost could incorporate into their installations the production line required to develop the process of the invention. Moreover, the solid by-product obtained can be fed, for example, into the sauce production line.

In another specific embodiment of the process of the invention, the extractant lipid is a natural or synthetic fat or oil, of food and/or pharmaceutical grade, or a combination thereof.

As an extractant agent, any lipid, fat, oil or mixture thereof can be used, in which lycopene is soluble and which is authorized by food and/or pharmaceutical regulations of the country in which the product is to be marketed.

In a preferred embodiment, the extractant lipid is a vegetal oil. In a more preferred embodiment, the extractant lipid is a vegetal oil selected from the group that includes olive oil, sunflower oil, soya oil, rapeseed oil, palm oil, walnut oil, almond oil and linseed oil.

In another preferred embodiment, the extractant lipid is an animal oil. In a more preferred embodiment, the extractant lipid is an animal oil selected from oily fish oil (dark fish oil) and cod-liver oil.

In another preferred embodiment, the extractant lipid is a fat selected from vaseline and glycerine.

Another aspect of the invention refers to a lycopene-enriched formulation free of organic solvents obtainable by the process described that comprises lycopene at a concentration of 1000 ppm or less and a lipid of food and/or pharmaceutical grade (herein referred to as the "formulation of the invention").

In a preferred embodiment, the formulation of the invention includes lycopene in a concentration of 500 ppm and olive oil.

As an example, the lycopene concentration in a formulation obtained from tomato concentrate by the process of the invention can be 500 ppm, i.e. 500 mg of lycopene per kg of formulation, depending on the variety of tomato used and the conditions applied, while in fresh tomatoes the lycopene content is around 30-50 mg per kg of tomato (30-50 ppm).

Figure 1:
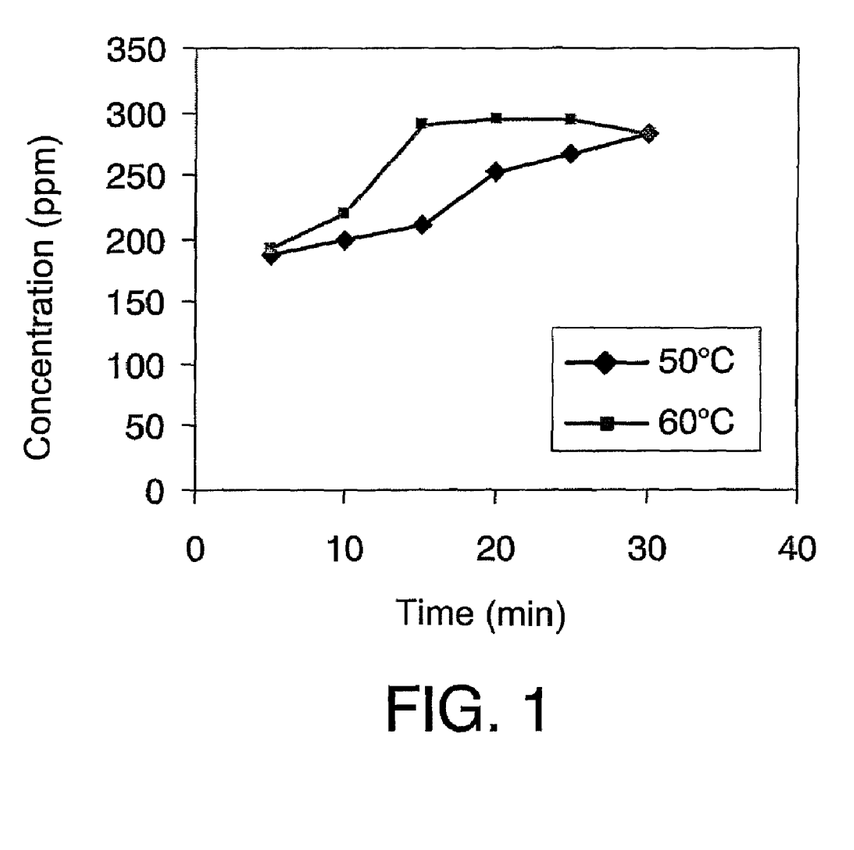
FIG. 1 shows the concentration of lycopene extracted with olive oil as a function of time, using two different temperatures.

The lycopene concentration in the formulation depends on the water and lycopene contents of the lycopene source, the temperature, the contact time and the ratio of the lipid/lycopene source. An expert can easily modify these variables to obtain the desired lycopene concentration. As an example, FIG. 1 shows the extraction kinetics of lycopene with olive oil at two temperatures. In both cases, it can be observed that the extraction process is very rapid, and the extraction takes place from the first moment, increasing with the time of contact to reach a more or less constant value. A rapid extraction kinetics is beneficial from a practical perspective, since it permits high production rates at an industrial level.

Figure 2:
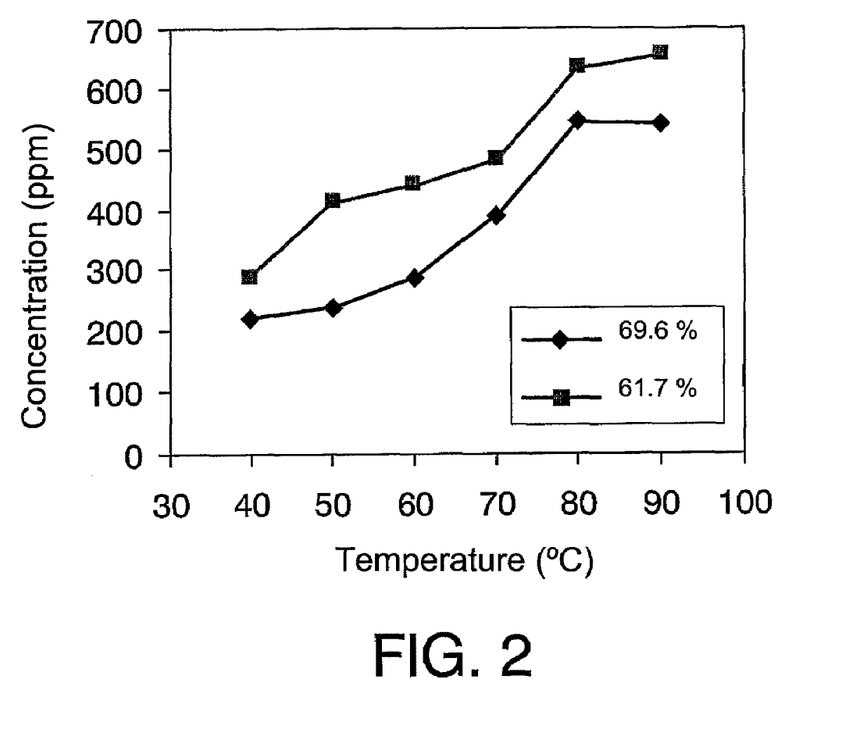
FIG. 2 shows the concentration of lycopene extracted with olive oil as a function of the temperature, using two sources of lycopene with different moisture content for an extraction time of 10 minutes.

FIG. 2 shows the influence of temperature and moisture content of the lycopene source in the extraction process of lycopene with olive oil (extraction time: 10 min). It can be observed that a reduced water content favors the extraction. Moreover, as the temperature rises, the lycopene concentration of the formulation also rises. It is recommendable to not use high temperatures (not over 120° C.) to avoid heat degradation of the formulation.

In the process of the invention, other phytochemicals are also extracted (carotenoids, sterols, etc.) which also have an antioxidant potential. This is important from a practical perspective since it has been demonstrated that the beneficial effects of antioxidants is enhanced by the synergic effects between them. For example, it has been shown that the beneficial effect of vitamin E is enhanced when this is present in natural oils (for example, olive oil), and this is believed to be due to the synergic effect with phytosterols. For this reason, the formulations obtained by the process of the invention are nutritionally more beneficial than those obtained by simply mixing the pure lycopene with oil or fat. In a specific embodiment, when the lycopene source corresponds to tomato concentrate, a considerable number of carotenoids are extracted, which are naturally present in tomatoes, although at lower concentrations:

|  | Lycopene | β-carotene | Phytoene | Neurosporene |
|---|---|---|---|---|
| Concentration: (ppm) | 541 | 102 | 90 | 68 |

As an example, to demonstrate the antioxidant capacity of lycopene in combination with the other phytochemicals extracted in the formulations obtained, the oxidative stability of a sample of olive oil has been assessed and also that of a formulation obtained by the process of the invention, consisting in olive oil and 600 ppm of lycopene. This measurement of oxidative stability was done using the process accelerated using a Rancimat 743, heating the samples to 100° C. under oxygen saturation. This apparatus measures the induction period of the oxidation reaction in hours. The results obtained are shown in Table 1.

TABLE 1

Rancimat analysis

| Sample | Assay | Time (h) |
|---|---|---|
| Olive oil | 1 | 8.0 |
|  | 2 | 8.3 |
|  | Mean | 8.15 |
| Formulation | 1 | 22.5 |
|  | 2 | 21.8 |
|  | Mean | 22.15 |

It can be observed that the formulation of the invention containing olive oil and lycopene presents an oxidative stability that is almost three times higher than the oxidative stability of olive oil alone.

Another important aspect to take into account is that the lycopene from the processed tomato products presents a greater bioavailability than the lycopene in fresh tomatoes, since all the lycopene in the trans form is transformed into lycopene in the cis form by heating in the presence of food lipids (Agarwal S. and Rao A. V. (2000), "Tomato lycopene and its role in human health and chronic diseases", *Can. Med. Assoc. J.* 163, 739-744). In the formulations provided by the invention, absorption is favored by the fact that the lycopene is dissolved in lipids (Bohm V. (2002), "Intestinal absorption of lycopene from different types of oleoresin capsules". *J. Food Sci.* 67, 1910-1913).

The lycopene-enriched formulation free of organic solvents provided by this invention has antioxidant and colorant properties, is easy to absorb and can be used to make compositions that comprises these concentrates.

In another aspect of the invention, a composition is provided that comprises the formulation of the invention and, also, one or more diluents and/or additives (herein referred to as the "composition of the invention").

In a particular embodiment of the composition of the invention, the diluent or diluents, of food and/or pharmaceutical grade, are selected from: olive oil, oily fish oil, cod liver oil and linseed oil.

As a diluent, olive oil is preferred, and preferably, extra virgin olive oil, since this is a natural product that can be obtained by simple mechanical compression, without requiring solvents and has an important concentration of tocopherols. The latter are compounds with antioxidants properties that exert a synergic effect with the lycopene present in the composition of the invention, as mentioned previously. Moreover, several studies have demonstrated that olive oil has a preventive effect against cardiovascular diseases. In fact, olive oil labels in the United States can show the following message: "Scientific tests have shown that taking two spoonfuls of olive oil a day reduces the risk of coronary diseases". Hence, the lycopene-enriched formulation with virgin olive oil would correspond to a natural product obtained without any chemical treatment, with the resulting commercial revaluation.

Therefore, in a preferred embodiment, this diluent is an oil with a high content of omega-3 fatty acids, such as cod liver oil, oily fish oil and linseed oil. These fatty acids have a beneficial effect on health and can help to prevent coronary diseases, and this effect is reinforced by the presence of lycopene.

In another specific embodiment of the composition of the invention, additives are selected from antioxidants, emulsifiers and mixtures thereof. As an antioxidant, any antioxidant agent can be used that is authorized by the food and/or pharmaceutical regulations of the country in which the product is to be marketed. Likewise, as an emulsifier, any emulsifying agent can be used that is authorized by the food and/or pharmaceutical regulations of the country in which the product is to be marketed.

In a preferred embodiment, the antioxidants are selected from ascorbic acid and tocopherol.

In another preferred embodiment, the emulsifiers are selected from lecithin and monoglycerides.

Hence, the formulation of the invention can be used in the form that it is produced, or can be diluted with a diluent to give the desired concentration of lycopene, or, optionally, one or more appropriate additives can be added, such as, for example, antioxidants emulsifiers and mixtures thereof.

The formulation or the composition of the invention can contain a variable amount of lycopene, depending on its intended application. Also, the diluent and the additives, when these are used, can be present in the composition of the invention in variable amounts depending on its proposed function.

In another aspect of the invention, the use of a formulation or a composition as described previously is provided to make nutraceutical, cosmetic, pharmaceutical or food products.

The formulations or the compositions of the invention can be used to make different food products such as mayonnaise, salad dressings, sauces, margarines etc. Hence, the formulation rich in olive oil with 500 ppm of lycopene described previously, can be either consumed directly or used in salad dressings.

Moreover, the formulations or the compositions of the invention can be used in the cosmetics industry. It should be taken into account that free radicals are not only formed inside the organism, but can also be produced in the skin due to numerous environmental factors such as smoke or ultraviolet radiation from the sun. It has been demonstrated that the antioxidant activity of phytochemicals, not only has a protective effect at the cellular level but also at a cutaneous level (S. R. Pinnell (2003), "Cutaneous photodamage, oxidative stress, and topical antioxidant protection", *J. Am. Acad. Dermatol.* 48(1), 1-19). For this reason, given the antioxidant potential of lycopene, creams, lotions and other cosmetics are being launched onto the market that incorporate, as a new ingredient, this carotenoid in their composition such as, for example, those marketed by the firm Kiehl's.

Therefore, the formulations or the compositions of the invention can take any presentation form, liquid or solid, such as, for example, encapsulated in soft gelatin capsules. These capsules are suitable for direct consumption by the consumer.

In the specific case of the encapsulated formulation, this must be encapsulated under nitrogen, following the usual methods (Faulí C. (1993), "Cápsulas de gelatina blandas", in *Tratado de Farmacia Galénica*, 1ª ed., Luzán 5, S. A. de Ediciones, page. 587-592), in soft gelatin capsules that should be colored in order to prevent their degradation from sunlight. All the products obtained should be packaged under nitrogen in opaque containers that protect them from the effects of exposure to sunlight.

Although there is no absolute agreement about the daily recommended amount of lycopene, epidemiological studies indicate that even low concentrations have a beneficial effect. For example, diets with lycopene supplements between 2.5 mg and 5 mg a day, appear to have a protective effect against cardiovascular diseases (Most M. (2004), "Estimated phytochemical content approaches to stop hypertension (DASH) diet is higher than in the control study diet", *J. Am. Diet Assoc.*, 104, 1725-1727). An intake of 10 g (normal dose in a salad dressing) of the formulation of the invention with a concentration of 500 ppm provides a total of 5 mg. On the other hand, the different studies carried out indicate that relatively high concentrations (>30 ppm/day) are not harmful to health. Therefore, the manufacturer has a wide range of concentrations for preparing their products, depending on their preferences or commercial interests.

An additional advantage of the products provided by this invention, both of formulations of the invention and the compositions comprising them, lies in the fact that, in contrast to natural sources of lycopene, these facilitate the absorption of lycopene in the intestinal tract. Indeed, in natural sources of lycopene, such as tomatoes, this pigment is occluded in the chromoplasts, cellular organelles surrounded by a wall, which makes it more difficult its absorption in the intestine. Studies carried out by Drs. W. Stahl and H. Sies, of the University of Dusseldorf, demonstrate how the presence of an oil greatly increases the absorption of lycopene (Stahl, W. and Sies H. (1996), *Archives of Biochemistry and Biophysics*, 336(1)). As indicated previously, this is because in natural sources, lycopene is in the trans form and occluded in the chromoplasts.

This invention can be of interest to the tomato concentrate industry since this product is a magnificent raw material for the process, as mentioned previously. The lycopene-enriched formulation free of organic solvents provided by this invention and the compositions that contain it, are mainly designed for the nutraceutical industry, conferring it an added value and making it an important source of revenue for the industry. Moreover, as mentioned previously, the formulations of the invention can be used to make different products (mayonnaise, salad dressings, sauces, margarines, etc.) that will become new sources of lycopene in food products, with the consequent added value for the industry and the dietary advantages for the consumer.

Finally, it is noteworthy that the low cost of the process of the invention signifies that all the products can be offered at an affordable price for consumers. Currently, owing to their high price, lycopene-enriched products can only be afforded by consumers with high purchasing power. Therefore, by increasing the consumption among the population of a compound such as lycopene with so many beneficial properties, the application of the invention contributes to improving the nutritional grade of the population.

The following examples illustrate the invention and should not be considered as limiting its scope of application.

EXAMPLE 1

Preparation of Lycopene-Enriched Olive Oil Formulations Free of Organic Solvents for Direct Consumption as Salad Dressing This example describes the direct preparation of formulations of olive oil containing different concentrations of lycopene from tomato concentrate with 61.7% moisture content by weight.

The olive oil and tomato concentrate are mixed together in a weight proportion of 1:1 in a discontinuous industrial mixer, thermostatized, at 4500 r.p.m. for 5 minutes at different temperatures. Then, the two phases are separated by centrifuging at 4000 r.p.m. The liquid phase is a formulation of lycopene-enriched olive oil free of organic solvents. Table 1 shows, for each temperature, the lycopene concentration in each of the oil formulations, and the amount of lycopene in 10 g of the formulation (normal intake in a salad dressing).

It should be protected from sunlight at all times since lycopene is photosensitive. For this reason, lycopene-enriched oil can be packaged in an opaque container or in a topaz-colored glass container.

TABLE 1

| | Lycopene content | |
|---|---|---|
| Temperature (° C.) | Concentration in the formulation (ppm) | mg lycopene/10 g formulation |
| 40 | 290 | 2.9 |
| 50 | 414 | 4.1 |
| 60 | 438 | 4.4 |
| 70 | 479 | 4.8 |
| 80 | 633 | 6.3 |
| 90 | 656 | 6.6 |

It can be observed that several lycopene-enriched olive oil formulations free of organic solvents can be obtained simply and rapidly. These formulations present an adequate amount of lycopene for easy and safe dosification for the purpose of providing a suitable daily dose of lycopene.

EXAMPLE 2

Preparation of Lycopene-Enriched Sunflower Oil Formulations Free of Organic Solvents to Prepare Mayonnaise.

In this example, the direct preparation of sunflower oil formulations with different lycopene concentrations obtained from a tomato concentrate with 61.7% moisture content by weight is described:

The sunflower oil is mixed with the tomato concentrate in a weight proportion of 1:1 in a discontinuous industrial mixer, thermostatized, at 4500 r.p.m. for 5 minutes and at different temperatures. Afterwards, the two phases are separated by centrifuging at 4000 r.p.m. The liquid phase, which corresponds to lycopene-enriched sunflower oil free of organic solvents, is used as a base to prepare mayonnaise according to the following formulation:

| | |
|---|---|
| Sunflower oil | 70.0% |
| Eggs | 28.5% |
| Vinager | 1.0% |
| Salt | 0.5% |

Table 2 shows, for each temperature, the concentration of lycopene in each of the oil formulations, and the amount of lycopene in a 10 g dose of mayonnaise.

TABLE 2

| | Lycopene contents | |
|---|---|---|
| Temperature (° C.) | Concentration of the formulation (ppm) | mg lycopene/10 g mayonnaise |
| 40 | 202 | 1.4 |
| 50 | 227 | 1.6 |
| 60 | 364 | 2.5 |
| 70 | 500 | 3.4 |
| 80 | 636 | 4.4 |
| 90 | 756 | 5.2 |

Following this process, different formulations of lycopene-enriched sunflower oil free of organic solvents can be obtained simply and rapidly. These formulations can be used directly in the preparation of a mayonnaise which, therefore, becomes a lycopene source.

EXAMPLE 3

Preparation of a Lycopene-Enriched Vaseline Formulation Free of Organic Solvents to Prepare Cosmetic Creams.

In this example, the direct preparation of a formulation of vaseline is described with different concentrations of lycopene obtained from a tomato concentrate with 69.6% moisture content by weight.

The tomato concentrate and the vaseline are mixed together in proportions of 1:2, 1:1 and 2:1 by weight in a discontinuous industrial mixer, thermostatized at 70° C., at 3000 r.p.m. for 1 minute. Then, the two phases are separated by centrifugation at 4000 r.p.m. The liquid phase, which is lycopene-enriched vaseline free of organic solvents, is used as a base to prepare a regenerating cosmetic cream and a moisturizing cosmetic cream, with proportions of vaseline of 12% and 20% by weight, respectively.

Table 3 shows, for each proportion of tomato concentrate and vaseline, the lycopene concentration in the formulation and the amount of lycopene present in a 100 g dose of cosmetic cream.

TABLE 3

| | Lycopene content | | |
|---|---|---|---|
| Tomato conc/ Vaseline (g/g) | Concentration in the formula (ppm) | mg lycopene/100 g regenerating cream | mg lycopene/ 100 g moisturizing cream |
| 1/2 | 82 | 1.0 | 1.6 |
| 1/1 | 113 | 1.4 | 2.3 |
| 2/1 | 140 | 1.7 | 2.8 |

It can be observed that a formulation of lycopene-enriched vaseline free of organic solvents can be obtained simply and rapidly. This formulation can be used directly to prepare cosmetic creams.

The invention claimed is:

1. A process to obtain a lycopene-enriched formulation free of organic solvents that comprises:
   (a) mixing a lycopene source with an extractant lipid; and
   (b) separating the lipidic phase obtained in step (a) to obtain the lycopene-enriched formulation free of organic solvents;
   characterized in that the mixture in step (a) is carried out in the absence of organic solvents.

2. Process according to claim 1, characterized in that in step (a) the lycopene source and the extractant lipid are mixed by stuffing at high speed at a temperature below 120° C.

3. Process according to claim 2, characterized in that the speed of stirring varies between 500 and 10000 r.p.m. and the temperature between 40 and 100° C.

4. Process according to claim 3, characterized in that the speed of stirring varies between 2500 and 5000 r.p.m. and the temperature between 60 and 90° C.

5. Process according to claim 1, characterized in that step (a) is carried out under vacuum or an inert atmosphere.

6. Process according to claim 1, characterized in that it comprises a previous step of dehydration of the lycopene source.

7. Process according to claim 1, characterized in that the lycopene source is a plant product, algae or microorganism that contains lycopene.

8. Process according to claim 7, characterized in that the product that contains lycopene is a plant product.

9. Process according to claim 8, characterized in that it is a plant product derived from tomato selected from the group consisting of completely dehydrated tomato, partially dehydrated tomato, tomato concentrate, powdered tomato and lyophilized tomato.

10. Process according to claim 1, characterized in that the extractant lipid is a natural or synthetic fat or oil, of food and/or pharmaceutical grade, or a mixture thereof.

11. Process according to claim 10, characterized in that the oil is a vegetable oil.

12. Process according to claim 11, characterized in that the oil is selected from the group consisting of olive oil, sunflower oil, soya oil, rapeseed oil, palm oil, walnut oil, almond oil and linseed oil.

13. Process according to claim 10, characterized in that the oil is an animal oil.

14. Process according to claim 13, characterized in that the oil is selected from oily fish oil and cod liver oil.

15. Process according to claim 10, characterized in that the oil is selected from vaseline and glycerine.

* * * * *